United States Patent
Ambrosio

(10) Patent No.: US 9,782,300 B2
(45) Date of Patent: Oct. 10, 2017

(54) FIBER-MICROSPHERE BIORESORBABLE COMPOSITE SCAFFOLD FOR WOUND HEALING

(75) Inventor: Archel Ambrosio, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 392 days.

(21) Appl. No.: 12/012,274

(22) Filed: Feb. 1, 2008

(65) Prior Publication Data
US 2009/0198167 A1    Aug. 6, 2009

(51) Int. Cl.
| | |
|---|---|
| A61F 13/00 | (2006.01) |
| A61M 1/00 | (2006.01) |
| A61F 13/02 | (2006.01) |
| A61K 9/70 | (2006.01) |
| A61L 15/16 | (2006.01) |

(52) U.S. Cl.
CPC ......... *A61F 13/0203* (2013.01); *A61K 9/70* (2013.01); *A61L 15/16* (2013.01); *A61M 1/00* (2013.01); *A61M 1/0023* (2013.01); *A61M 1/0088* (2013.01); *A61F 13/00987* (2013.01)

(58) Field of Classification Search
CPC ......... A61K 9/70; A61K 9/7023; A61F 13/00; A61F 13/00987; A61F 13/00991; A61F 13/00995; A61L 15/00; A61L 15/16; A61L 15/18; A61L 15/20; A61M 1/00; A61M 1/0023; A61M 1/10; A61M 1/1037
USPC ..... 602/41–59; 424/443, 444; 428/364, 372, 428/373, 374; 604/327, 332, 335, 337
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Keri J Nelson

(57) ABSTRACT

A fiber-microsphere composite scaffold including a first layer of material selected from one of a layer of bioresorbable microspheres and a layer of bioresorbable fibers; and a second layer of material selected from the other of the layer of bioresorbable microspheres and the layer of bioresorbable fibers. A fiber-microsphere composite scaffold reduced pressure tissue treatment apparatus is also included as well as methods for making fiber-microsphere composite scaffolds.

21 Claims, 5 Drawing Sheets

(56) References Cited

U.S. PATENT DOCUMENTS

| | | |
|---|---|---|
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,213,812 A | 5/1993 | Ruiz |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,698,322 A * | 12/1997 | Tsai et al. ............ 428/373 |
| 5,766,631 A * | 6/1998 | Arnold ............ 424/486 |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,685,681 B2 * | 2/2004 | Lockwood et al. .......... 604/305 |
| 6,814,079 B2 | 11/2004 | Heaton et al. |
| 7,041,868 B2 * | 5/2006 | Greene et al. ............ 602/48 |
| 7,198,046 B1 * | 4/2007 | Argenta et al. ............ 128/897 |
| 2002/0016625 A1 | 2/2002 | Falotico et al. |
| 2002/0077661 A1 | 6/2002 | Saadat |
| 2002/0111576 A1 | 8/2002 | Greene et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0003127 A1 * | 1/2003 | Brown ............ A61L 27/42 424/423 |
| 2005/0118238 A1 | 6/2005 | Zhu et al. |
| 2005/0123588 A1 * | 6/2005 | Zhu et al. ............ 424/443 |
| 2006/0173253 A1 * | 8/2006 | Ganapathy et al. .......... 600/310 |
| 2007/0238167 A1 * | 10/2007 | Perez ............ C12N 5/0068 435/325 |
| 2009/0177133 A1 * | 7/2009 | Kieswetter et al. ............ 602/48 |
| 2011/0022085 A1 | 1/2011 | Murphy et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 01/10421 A1 | 2/2001 |
| WO | WO 2006/087021 A1 | 8/2006 |
| WO | WO 2007/092405 A2 | 8/2007 |
| WO | WO 2007/120617 A2 | 10/2007 |
| WO | WO 2009/088926 A1 | 7/2009 |

OTHER PUBLICATIONS

K.F. Jeter, T.E. Tintle, and M. Chariker, "Managing Draining Wounds and Fistulae: New and Established Methods," *Chronic*

(56) References Cited

OTHER PUBLICATIONS

*Wound Care*, edited by D. Krasner (Health Management Publications, Inc., King of Prussia, PA 1990), pp. 240-246.

G. Živadinović, V. Đukić, Ž. Maksimović, Đ. Radak, and P. Paška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

International Search Report and Written Opinion dated Mar. 11, 2009; PCT International Patent Application No. PCT/US2009/032648.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

\* cited by examiner

FIBER-MICROSPHERE BIORESORBABLE COMPOSITE SCAFFOLD FOR WOUND HEALING

BACKGROUND OF THE INVENTION

1. Field of the Invention

The present invention relates generally to dressings and scaffolds for wound healing and more specifically to fiber-microsphere composite bioresorbable wound dressings and scaffolds.

2. Description of Related Art

Advances in materials science has led to the development of materials for wound scaffolds and dressings that function to support and protect soft tissues that are slowly resorbed by the body for the convenience and comfort of a patient. The wound scaffolds and dressings are resorbed through chemical and biological processes of the body of a patient, thus eliminating the additional painful process of removing these wound scaffolds and dressings, which are oftentimes partially or wholly attached to the soft tissue itself.

A recent development to wound healing therapy has been the advent of reduced pressure tissue treatment, where a wound scaffold or dressing is applied to an affected area and a reduced pressure is applied to the wound scaffold or dressing to enhance the removal of wound fluids from the wound area and induce granulation tissue formation. Effectively applying such a reduced pressure requires that the wound scaffold or dressing maintain a certain level of porosity to be able to provide fluid flow-through capabilities during the therapy. Conventional wound scaffolds and dressings, such as gauze and the like, tend to compact between the reduced pressure manifold and the soft tissue, thus significantly decreasing the porosity of the scaffold or dressing. Sponge type material is in use as well for such therapies, yet their composition is not of a material that is bioresorbable, thus they must be removed or replaced from the tissue site from time to time, which may cause some discomfort to a patient.

BRIEF SUMMARY OF THE INVENTION

The problems presented by existing scaffolds and dressings are solved by a fiber-microsphere composite scaffold according to an illustrative embodiment of the invention. The fiber-microsphere composite scaffold includes a first layer of either a resorbable microsphere material or a resorbable fiber material adjacent to a second layer of the other resorbable microsphere material or resorbable fiber material. The fiber-microsphere composite scaffold provides for exudation of the tissue site while preventing complete compression of the fiber-microsphere composite scaffold. When used with a reduced pressure tissue treatment system, the fiber-microsphere composite scaffold provides for good support and flexibility while preventing complete compression and therefore occlusion of the pores of the fiber-microsphere composite scaffold to facilitate the exudation of the wound fluids from the tissue site.

The microsphere material provides thickness and porosity and the fiber material provides support and containment for the microsphere material within the fiber-microsphere composite scaffold. The combination of the alternating layers of fiber material and microsphere material provides for improved flexibility and exudation through the thickness of the microspheres combined with the flexibility and containment of the fiber material. This combination of layers of materials provides good flow of exudated wound fluids while maintaining some resistance to compression through use or reduced pressure. This combination minimizes compression of the fiber-microsphere composite scaffold during use, such as during reduced pressure tissue treatment.

One illustrative embodiment includes a fiber-microsphere composite scaffold including a first layer of material selected from one of a layer of bioresorbable microspheres and a layer of bioresorbable fibers; and a second layer of material selected from the other of the layer of bioresorbable microspheres and the layer of bioresorbable fibers. Another illustrative embodiment includes a fiber-microsphere composite scaffold reduced pressure tissue treatment apparatus. Yet another illustrative embodiment includes methods for making fiber-microsphere composite scaffolds.

Other objects, features, and advantages of the illustrative embodiments will become apparent with reference to the drawings and detailed description that follow.

DETAILED DESCRIPTION OF THE PREFERRED EMBODIMENT

Figure 1:
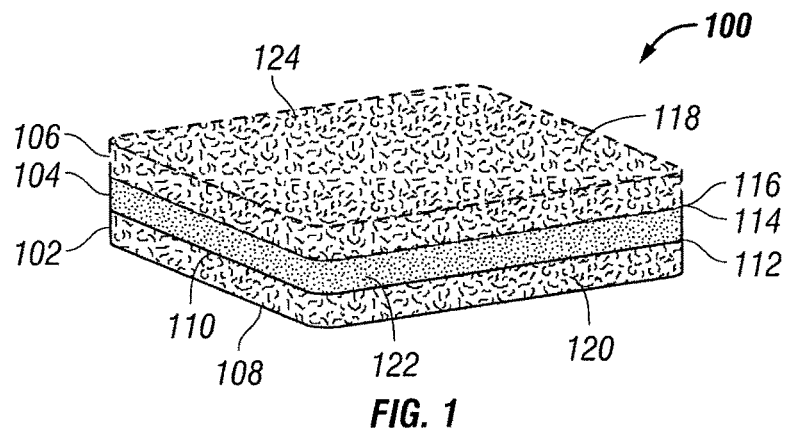
FIG. 1 illustrates a perspective view of a fiber-microsphere composite scaffold according to an illustrative embodiment of the invention.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "reduced pressure" may be used to describe the pressure applied to the tissue site, the actual pressure applied to the tissue site may be significantly less than the pressure normally associated with a complete vacuum. Reduced pressure may initially generate fluid flow in the tube and the area of the tissue site. As the hydrostatic pressure around the tissue site approaches the desired reduced pressure, the flow may subside, and the reduced pressure is then maintained. Unless otherwise indicated, values of pressure stated herein are gauge pressures.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "surface" as used herein refers to all or a portion of a surface comprising the plane of a particular material. The term "layer" as used herein generally refers to all or a portion of a particular layer of material. For example, a microsphere layer refers to a layer of material that includes microspheres. Moreover, the term "layer" should be understood to describe almost any shape or form of a material, but commonly will refer to a material that is in the shape of a continuous or discontinuous sheet or film of almost any thickness and degree of regularity or irregularity. A layer may comprise one material, or two or more materials.

The present fiber-microsphere composite scaffold may be used on different types of wounds or tissues, such as surface wounds, deep-tissue wounds, and subcutaneous wounds. For example, the fiber-microsphere composite scaffold may be placed adjacent to a bone of a patient and then the skin of the patient may be closed.

Figure 4:
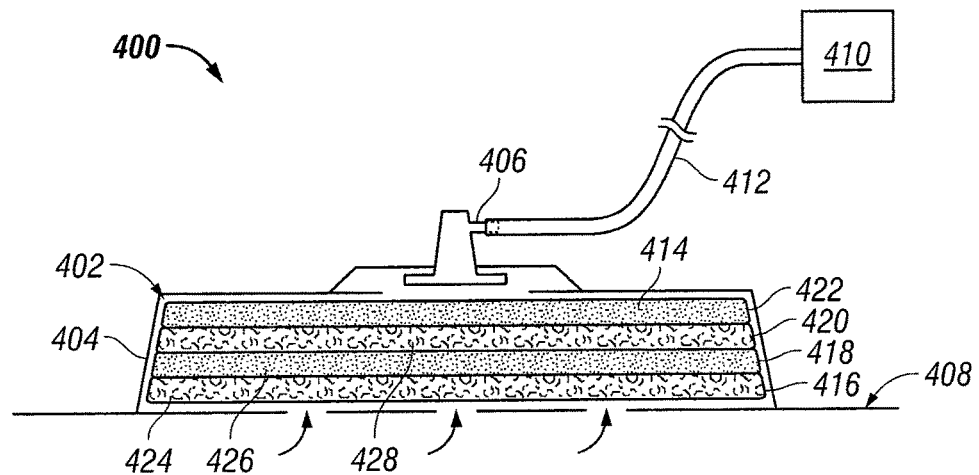
FIG. 4 illustrates a cross section view of a fiber-microsphere composite scaffold reduced pressure tissue treatment apparatus according to an illustrative embodiment of the invention.
Figure 5:
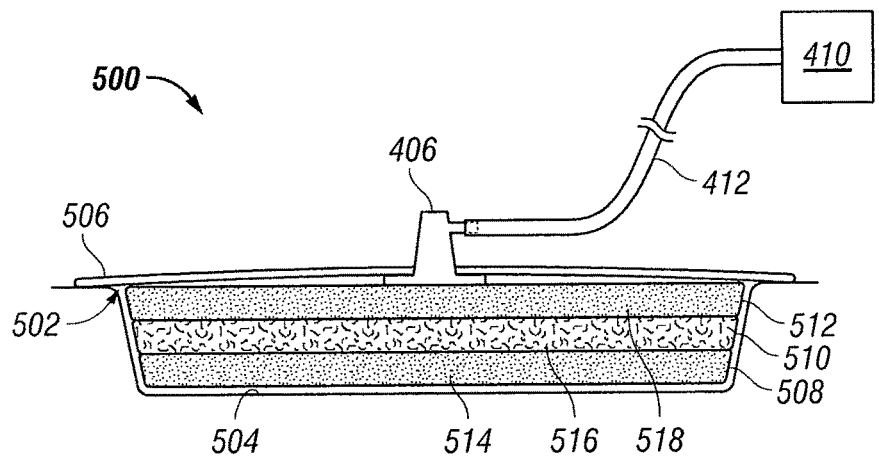
FIG. 5 illustrates a cross section view of a fiber-microsphere composite scaffold reduced pressure tissue treatment apparatus according to another illustrative embodiment of the invention.
Figure 6:
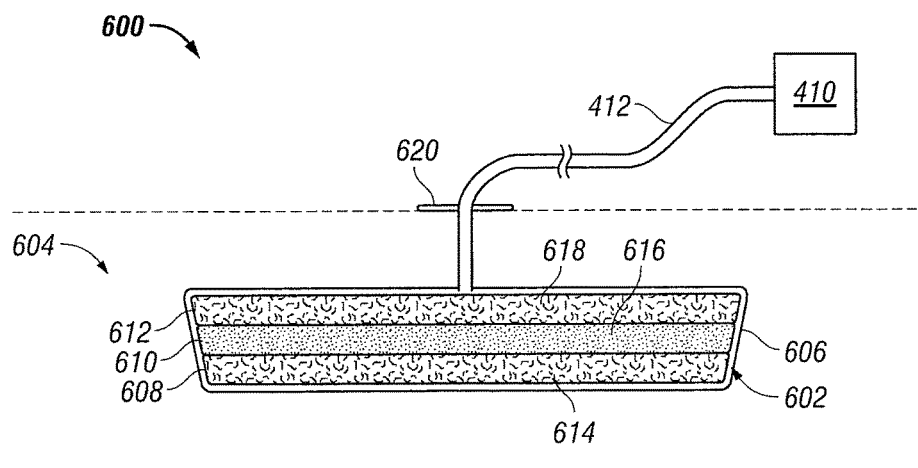
FIG. 6 illustrates a cross section view of a fiber-microsphere composite scaffold reduced pressure tissue treatment apparatus according to another illustrative embodiment of the invention.

Referring to FIG. 1, an illustrative embodiment of a fiber-microsphere composite scaffold 100 is shown. In this embodiment, the fiber-microsphere composite scaffold 100 has a first layer of fiber material, fiber layer 102, adjacent to a second layer of microsphere material, microsphere layer 104. The fiber layer 102 is also adjacent to a tissue site 408, 504, and 604 (FIGS. 4-6). The fiber layer 102 includes a first surface 108 and a second surface 110. In this embodiment, the first surface 108 of the fiber layer 102 may be adjacent to the tissue site 408, 504, and 604. The microsphere layer 104 includes a first surface 112 and a second surface 114. In this embodiment the second surface 110 of the fiber layer 102 is adjacent to the first surface 112 of the microsphere layer 104. In addition, the fiber-microsphere composite scaffold 100 may also include one or more additional layers of material, such as fiber layer 106. Although only one additional layer of fiber is shown, any number of additional layers of fiber may be used. Fiber layer 106 includes a second surface 118 and a first surface 116. The first surface 116 of the fiber layer 106 is adjacent to the second surface 114 of the microsphere layer 104. Fiber-microsphere composite scaffold 100 further includes flow channels 120, flow channels 122, and flow channels 124 for allowing exudates to flow between the layers.

Figure 2:
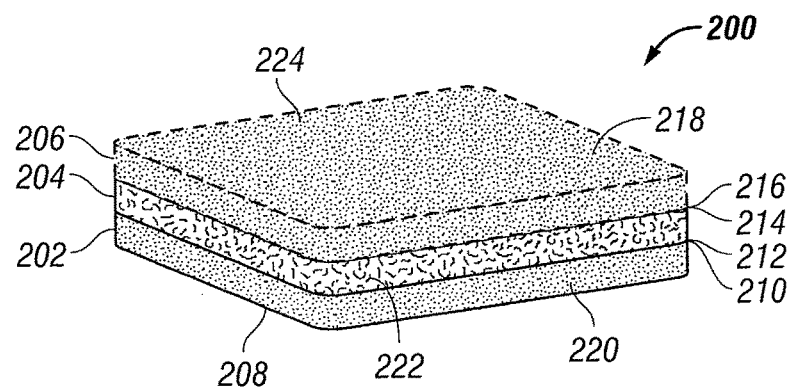
FIG. 2 illustrates a perspective view of a fiber-microsphere composite scaffold according to another illustrative embodiment of the invention.

FIG. 2 illustrates an illustrative embodiment of a fiber-microsphere composite scaffold 200 having multiple layers. Fiber-microsphere composite scaffold 200 includes a first layer of microsphere material, microsphere layer 202, adjacent to a second layer of fiber material, fiber layer 204. The microsphere layer 202 may be disposed adjacent to the tissue site 408, 504, and 604. The microsphere layer 202 includes a first surface 208 and a second surface 210. In this embodiment, the first surface 208 of the microsphere layer 202 may be adjacent to the tissue site 408, 504, and 604. The fiber layer 204 includes a first surface 212 and a second surface 214. In this embodiment, the second surface 210 of the microsphere layer 202 is adjacent to the first surface 212 of the fiber layer 204. Additionally, the fiber-microsphere composite scaffold 200 may include one or more additional layers of material, such as microsphere layer 206. Although only one additional layer of microsphere material is shown, any number of additional layers of microsphere material may be used. The microsphere layer 206 includes a first surface 216 and a second surface 218. Fiber-microsphere composite scaffold 200 further includes flow channels 220, 222, and 224 for allowing exudates to flow between the layers.

Figure 3:
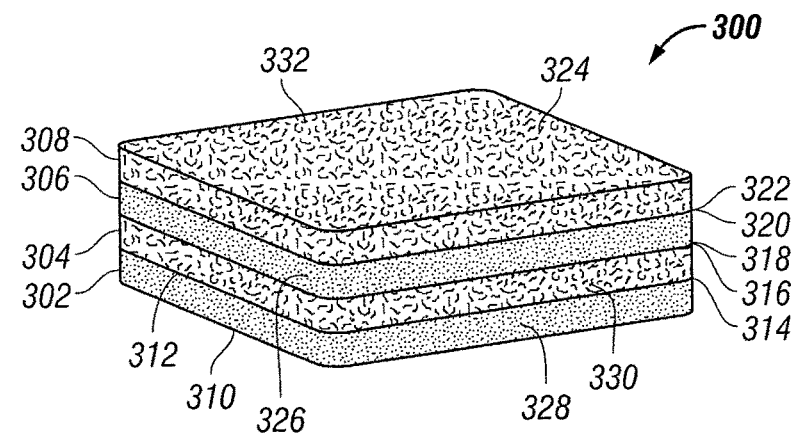
FIG. 3 illustrates a perspective view of a fiber-microsphere composite scaffold according to another illustrative embodiment of the invention.

FIG. 3 illustrates an illustrative embodiment of a fiber-microsphere composite scaffold 300 having an additional layer than that of fiber-microsphere composite scaffold 100 and fiber-microsphere composite scaffold 200. Fiber-microsphere composite scaffold 300 includes a first layer of microsphere material, microsphere layer 302, adjacent to a second layer of fiber material, fiber layer 304. The microsphere layer 302 may be disposed adjacent to the tissue site 408, 504, and 604. Alternatively, fiber layer 308 may be adjacent to the tissue site 408, 504, and 604 (not shown in FIG. 3). The microsphere layer 302 includes a first surface 310 and a second surface 312. The fiber layer 304 includes a first surface 314 and a second surface 316. In this embodiment, the second surface 312 of the microsphere layer 302 is typically adjacent to the first surface 314 of the fiber layer 304. Additionally, the fiber-microsphere composite scaffold 300 includes a third layer of microsphere material, microsphere layer 306, and a fourth layer of fiber material, fiber layer 308. Microsphere layer 306 includes a first surface 318 and a second surface 320; fiber layer 308 includes a first surface 322 and second surface 324. In this embodiment, second surface 316 is adjacent to first surface 318 and second surface 320 is adjacent to first surface 322. Fiber-microsphere composite scaffold 300 further includes flow channels 326, 328, 330, and 332.

In another illustrative embodiment of the fiber-microsphere composite scaffold 300, the four alternating layers of material are in the order of: fiber layer 304, microsphere layer 302, fiber layer 308, and microsphere layer 306, wherein the fiber layer 304 is positioned adjacent the tissue site.

FIG. 4 illustrates an illustrative embodiment of a reduced pressure tissue treatment system 400. The reduced pressure tissue treatment system 400 includes a fiber-microsphere composite scaffold 402 for insertion substantially adjacent a tissue site 408 and a wound drape 404 for sealing enclosure of the fiber-microsphere composite scaffold 402 and the tissue site 408. As shown, fiber-microsphere composite scaffold 402 includes a fiber layer 416, a microsphere layer 418, a fiber layer 420, and a microsphere layer 422. After insertion of the fiber-microsphere composite scaffold 402 into the tissue site 408 and sealing with the wound drape 404, the fiber-microsphere composite scaffold 402 is placed in fluid communication with a vacuum or reduced pressure source 410 to promote fluid drainage and stimulation of new tissue growth. A reduced pressure delivery tube 412 connects the reduced pressure source 410 to a tubing connector 406 that is typically placed in communication with the fiber-microsphere composite scaffold 402 and extends through the wound drape 404. Drainage and distribution of reduced pressure is facilitated by the flow channels 414, 424, 426, and 428 located in the fiber layer 416, microsphere layer 418, fiber layer 420, and microsphere layer 422, respectively.

The wound drape 404 may be impermeable or selectively permeable and preferably is constructed from an elastomeric material that at least peripherally is covered on at least one side with a pressure sensitive, acrylic adhesive for sealing the wound drape 404 over the tissue site 408.

FIG. 5 illustrates another illustrative embodiment of a reduced pressure tissue treatment system 500. The reduced pressure tissue treatment system 500 includes a fiber-microsphere composite scaffold 502 for insertion substantially adjacent a tissue site 504 and a drape 506 for sealing enclosure of the fiber-microsphere composite scaffold 502 and the tissue site 504. As shown, the fiber-microsphere composite scaffold 502 includes a microsphere layer 508, fiber layer 510, and microsphere layer 512. After insertion of the fiber-microsphere composite scaffold 502 into the tissue site 504, the drape 506 is sealed, and the fiber-microsphere composite scaffold 502 is placed in fluid communication with the reduced pressure source 410 for promotion of fluid drainage, as described above. The reduced pressure delivery tube 412 connects the reduced pressure source 410 to the tubing connector 406 that is typically placed in communication with the fiber-microsphere composite scaffold 502 and extends through the drape 506. Drainage and stimulation of new tissue growth are facilitated by flow channels 514, 516, and 518 located in the microsphere layer 508, fiber layer 510, and microsphere layer 512, respectively.

The reduced pressure tissue treatment apparatuses described herein are provided to administer reduced pressure tissue treatment to a tissue site of a living being. The tissue site 504 may include a burn or other wound, or alternatively may be healthy tissue upon which it is desired to promote new tissue growth. As shown in FIGS. 2, 3, and 5, the microsphere layer 202, microsphere layer 302, and microsphere layer 508 are adjacent to the tissue site. In these embodiments, the microsphere material layer conforms well to uneven surfaces, such as deep wound bodies and the like.

FIG. 6 illustrates another illustrative embodiment of a reduced pressure tissue treatment system 600. The reduced pressure tissue treatment system 600 includes a fiber-microsphere composite scaffold 602 for insertion substantially adjacent a subcutaneous tissue site 604 and for sealing enclosure of the fiber-microsphere composite scaffold 602 and the tissue site 604. As shown, the fiber-microsphere composite scaffold 602 includes a fiber layer 608, microsphere layer 610, and fiber layer 612. After insertion of the fiber-microsphere composite scaffold 602 into the tissue site 604, the tissue site 604 is substantially sealed, and the fiber-microsphere composite scaffold 602 is placed in fluid communication with the reduced pressure source 410 for promotion of fluid drainage, as described above. The reduced pressure delivery tube 412 connects the reduced pressure source 410 to the fiber-microsphere composite scaffold 602 to deliver reduced pressure to the tissue site 604. A seal 620 may be provided to assist in sealing around the reduced pressure delivery tube 412 where the tube enters the patient's body. Drainage and stimulation of new tissue growth are facilitated by the flow channels 614, 616, and 618 located in the fiber layer 608, microsphere layer 610, and fiber layer 612.

In another illustrative embodiment, the order of the layers of the fiber-microsphere composite scaffold 402, fiber-microsphere composite scaffold 502, and fiber-microsphere composite scaffold 602 may be in any order desired.

The fiber-microsphere composite scaffolds described herein may include additional layers of alternating material types in addition to those illustrated in FIGS. 1-6. For example, fiber-microsphere composite scaffold 200 may include a fourth or additional layers of material, such as another fiber layer above the microsphere layer 206. In another example, fiber-microsphere composite scaffold 100 may include a fourth or additional layers of material, such as a microsphere layer above the fiber layer 106. The fiber-microsphere composite scaffolds described herein may include any number of layers for a desired application. The additional layers may alternate between fiber layers and microsphere layers or the scaffolds may include adjacent layers of the same type of material.

The flow channels described herein may be created by voids and/or cells in the fiber and microsphere layers that are fluidly connected to or in communication with adjacent voids and/or cells. The flow channels may allow fluid communication throughout a particular layer of the fiber or microsphere material and between layers. The flow channels may be uniform in shape and size, or may include patterned or random variations in shape and size. Variations in shape and size of the voids and/or cells of the fiber and/or microsphere layers may be selectively chosen and used to alter the flow characteristics of fluid and/or exudates through the fiber and/or microsphere layers.

The flow channels described herein allow distribution of reduced pressure and/or transportation of exudates and fluids to and from a particular tissue site. The flow channels provided in each layer of material may be an inherent characteristic of the material, provided for example by the porosity of the layers, or the flow channels may be chemically, mechanically, or otherwise formed in the material prior to or after assembly of the layers of material of the fiber-microsphere composite scaffold. The placement of these layers of material adjacent to one another enables fluid communication between layers.

Regardless of whether pores, voids, apertures, or some other combination thereof are used to define the flow channels, the porosity of one layer of material, either fiber layer or microsphere layer, may be different than an adjacent layer of material to minimize in-growth of tissue into the adjacent layer of material. The porosity of one layer of material, either fiber layer or microsphere layer, may be controlled by limiting the size of the pores, voids, and/or apertures, or by controlling the number (i.e. density) of pores, voids, and/or apertures disposed in a particular layer of material.

The flow channels in the fiber layers may be formed by voids between the individual fibers. For fiber layers comprised of non-woven fibers, the sizing and spacing of the voids may be more random than with fiber layers comprised of woven fibers. The size and density of voids in fiber layers having woven fibers may be selectively controlled based on the tightness of the weave.

The flow channels in the microsphere layers may be formed by voids or spaces between the microspheres. The number and spacing of microspheres in any given microsphere layer will often determine the size and density of the voids.

The void, pore, or cell sizes of the fiber layers and microsphere layers described herein are preferably from about 50 microns to about 600 microns. In another illustrative embodiment, the pore size of the fiber layers and the microsphere layers may be from about 400 microns to about 600 microns. Since the microspheres in the microsphere layers may be adjacent to the fiber layers, it is desired that the voids, pores, or cells of the fiber layers be smaller in size than the size of the microspheres to prevent the microspheres from passing through the voids, pores, or cells of the fiber layers.

The layer of material, either fiber layer or microsphere layer, most distal from the tissue site typically will be the layer of material that is closest to the source of reduced pressure or vacuum applied in the fiber-microsphere composite scaffold reduced pressure tissue treatment apparatuses 400, 500, and 600. This layer of material may assist in distributing the reduced pressure or vacuum received from the reduced pressure 410 via reduced pressure delivery tube 412. This layer of material may further be used to distribute fluids that are introduced to the tissue site or to manifold wound exudates and other fluids collected from the tissue site. In one embodiment, this layer of material may be any porous material that is capable of accomplishing these tasks, and may not be limited to fiber or microsphere layers. For example, the distribution material may include without limitation devices that have structural elements arranged to form flow channels, such as open-cell cellular foams, porous tissue collections, and liquids, gels and other foams that include or cure to include flow channels.

Certain pores, voids, and/or apertures of the layers of material may be "closed" such that the pores, voids, and apertures are not fluidly connected to adjacent pores, voids, and apertures. These closed regions of a layer may be selectively combined with open regions to prevent transmission of fluids through selected portions of the fiber-microsphere composite scaffolds.

In any of the previous embodiments, an outside membrane layer may be used to protect the most outward layer of material from being contaminated prior to use. In one aspect, the outer membrane layer may be affixed or adhered to the present fiber-microsphere composite scaffold such that it is easily removed by a user prior to placing it a tissue site.

The scaffolds described herein may be substances or structures used to enhance or promote the growth of cells and/or the formation of tissue. The scaffolds are typically three dimensional porous structures that provide a template for cell growth. The scaffolds may be infused with, coated with, or comprised of cells, growth factors, or other nutrients to promote cell growth. A scaffold may be used as a manifold in accordance with the embodiments described herein to administer reduced pressure tissue treatment to a tissue site similar to tissue sites 408, 504, and 604.

The fiber-microsphere composite scaffolds described herein may be any particular thickness, but preferably have a thickness of from about 1 mm to about 30 mm. The thickness of the fiber-microsphere composite scaffolds is typically measured in a direction normal to the tissue site. The thickness of the individual layers comprising the fiber-microsphere composite scaffold may vary depending on the type of layer. For example, in one embodiment, the microsphere layer may have a thickness of between about 0.2 mm and about 1 mm. As another example, in one embodiment, the fiber layer may have a thickness of between about 0.1 mm and about 1 mm. The dimensions of the fiber-microsphere composite scaffolds in a plane normal to the thickness dimension may vary depending on the size of the tissue site. The fiber-microsphere composite scaffolds and individual fiber layers and microsphere layers may be provided in a large size and then trimmed or formed to fit the tissue site.

The fiber layers described herein may be comprised of continuous filaments or discreet elongated pieces, similar to thread-like materials. Some illustrative fibers include without limitation natural fibers, man-made fibers, mineral fibers, polymer fibers, and those fibers commonly known in the art as microfibers.

The fiber layers described herein may include a mesh of fibers in either a random, unorganized configuration as shown by the cross sections of FIGS. 1-6, or alternatively the fiber layers may comprise an organized fabric configuration also capable of supporting tissue ingrowth. The organized configuration is a fabric configuration which may be comprised of threads, yarns, nets, knits, weaves, laces, or felts of fibers. The fiber layers should be sufficiently open to allow infiltration of exudates and ingrowth of tissue through the open spaces between the fibers. In general, any bioabsorbable material may be suitable as a fiber material for the fiber layers as long as the mechanical properties and rate of bioabsorption are also appropriate for the intended application.

The fibers comprising the fiber layers may be spunbond, meltblown, or otherwise joined. Spunbond fibers are fibers that are formed by extruding molten thermoplastic material as filaments from a plurality of fine, usually circular capillaries of a spinnerette with the diameter of the extruded filaments then being rapidly reduced. Meltblown fibers are fibers that are formed by extruding molten thermoplastic material as filaments from a plurality of fine, usually circular, die capillaries as molten threads or filaments into a high velocity, usually heated gas (e.g., air) stream which attenuates the filaments of molten thermoplastic material to reduce their diameter. Thereafter, the meltblown fibers are carried by the high velocity gas stream and are deposited on a collecting surface to form a fabric of randomly disbursed meltblown fibers. Additionally, the fiber material may be woven or non-woven.

The dimensions of the fiber layers and microsphere layers of the fiber-microsphere composite scaffolds may be any size, thickness, surface area, or volume necessary to fit a desired application. In one embodiment, the fiber layers and microsphere layers may be formed in small sheets having desired thicknesses for a particular application. The fiber layers and microsphere layers may further be manufactured or formed in large sheets to span large tissue sites.

Microspheres may be obtained by various techniques, including by a solvent evaporation method. This method may be described as follows: the active principle to be encapsulated and the polymer which constitutes the microspheres are dissolved in a water-immiscible volatile organic solvent. In one illustrative embodiment, the microspheres may incorporate bioactive agents, such as drugs, growth factors, or other agents. The resulting solution is emulsified using a surface-active agent. Gradual evaporation of the organic solvent leads to the conversion of the droplets of the emulsion into solid microspheres in which the active principle is trapped.

The microspheres may be loose or joined. In one illustrative embodiment, the microspheres are sintered together. The sintering process includes heating the microspheres to a temperature that softens the material of the microspheres. The pressure of the sintering process is also dependent on the other process parameters, such as temperature and of material type of the microspheres.

The material composition of the fiber layers and microsphere layers described herein may be any bioresorbable material, including polymer-type materials. As used herein, the term bioresorbable generally means a material that slowly dissolves and/or digests in a living being, such as a human, and may be synonymous with bioabsorbable, biodissolvable, biodegradable, and the like. In one embodiment, bioresorbable may describe the property of a material, when the material is exposed to conditions that are typical of those present at a tissue site, to degrade into products that can be naturally removed from the tissue site within a period that substantially coincides with the period of wound healing. Such degradation products can be absorbed into the body of the patient or may be transmitted into another layer of the dressing. The period of wound healing is to be understood to be the period of time measured from the application of a dressing to the time that the wound is substantially healed. This period can range from a period of several days for simple skin abrasions on rapidly healing patients, to several months for chronic wounds on patients that heal more slowly. The dressings described herein may be fabricated so that the time required for bioresorption and/or bioabsorption of the scaffold material can be tailored to match the type of wound and the time necessary for healing. For example, in some dressings, the scaffold material may be designed to degrade within a period of one week, while in other dressings it may be designed to degrade within a period of one-to-three months, or even longer if desirable.

Typically, bioresorbable materials are broken down or metabolized by the body of a patient to smaller components that may ultimately be released from the body. A particular material may also be chosen based on the material's ability to support the growth of new tissue prior to resorption. Examples of suitable bioresorbable materials include without limitation polylactide ("PLA") (both L-lactide and D,L-lactide), copolymer of Poly(L-lactide-co-D,L-lactide), polyglycolic acid ("PGA"), alpha esters, saturated esters, unsaturated esters, orthoesters, carbonates, anhydrides, ethers, amides, saccharides, polyesters, polycarbonates, polycaprolactone ("PCL"), polytrimethylene carbonate ("PTMC"), polydioxanone ("PDO"), polyhydroxybutyrate, polyhydroxyvalerate, polydioxanone, polyorthoesters, polyphosphazenes, polyurethanes, collagen, hyaluronic acid, chitosan, hydroxyapatite, coralline apatite, calcium phosphate, calcium sulfate, calcium sulfate, calcium carbonate, carbonates, bioglass, allografts, autografts, and mixtures and/or co-polymers of these compounds. These compounds may be combined to produce co-polymers with fixed ratios of the polymers, such as 70:30 ratio of L-lactide-co-D,L-lactide. In addition, these compounds, polymers, and co-polymers may be linear or non-linear compounds.

In one illustrative embodiment, all or some of the layers of material, both fiber layers and microsphere layers, of the fiber-microsphere composite scaffold may be joined together to provide a unitary scaffold. For example, the alternating layers of material of the fiber-microsphere composite scaffold may be sintered together during manufacture. In another illustrative embodiment, all or some of the layers of material, both fiber layers and microsphere layers, of the fiber-microsphere composite scaffold may be bonded to each other. Bonding may be accomplished by heating all or some of the layers at their interfaces or surfaces and applying force to press the layers into a bonded connection. Alternatively, adhesives or mechanical fasteners may be used to connect the layers to one another as long as the fastening or bonding means does not substantially and negatively affect the distribution of pressure through the layers. For example, bioresorbable or biocompatible adhesives, such as fibrin adhesive, may be used to join the layers of material of the fiber-microsphere composite scaffold. In yet another illustrative embodiment, the layers of material may not be connected to one another, but rather, the layers of material may simply be placed in contact with one another prior to and/or during application of the reduced pressure tissue treatment or non-reduced pressure tissue treatment use. In yet still another illustrative embodiment, two of the layers of material may be bonded to one another, and a third or additional layers of material placed in contact with one of the two bonded layers.

Alternatively, the layers of material may be lightly bound together into a composite, multi-layer dressing prior to its application to the wound. Such binding may be accomplished by forming a second layer, such as for example, fiber layer, directly onto one side of a layer of a microsphere so that there will be points where the layers are bonded at the interface of the two layers. Thermal or ultrasonic pointbonding, as well as certain adhesives, may also be used to bond the layers of material. A feature of the interface between the layers of material is that it provides that the layers may be easily separated by the mere act of manually pulling a second layer from a first layer, for example, without disturbing the location of the first layer on the tissue site.

The addition of the microsphere layers to the fiber-microsphere composite scaffold resists collapsing of the fiber layers during application of reduced pressure. When the microspheres of the microsphere layers are either bonded together or attached to an adjacent fiber layer, the fiber-microsphere composite scaffold is capable of being trimmed or sized to fit a tissue site without substantially loss of individual microspheres.

Figure 7:
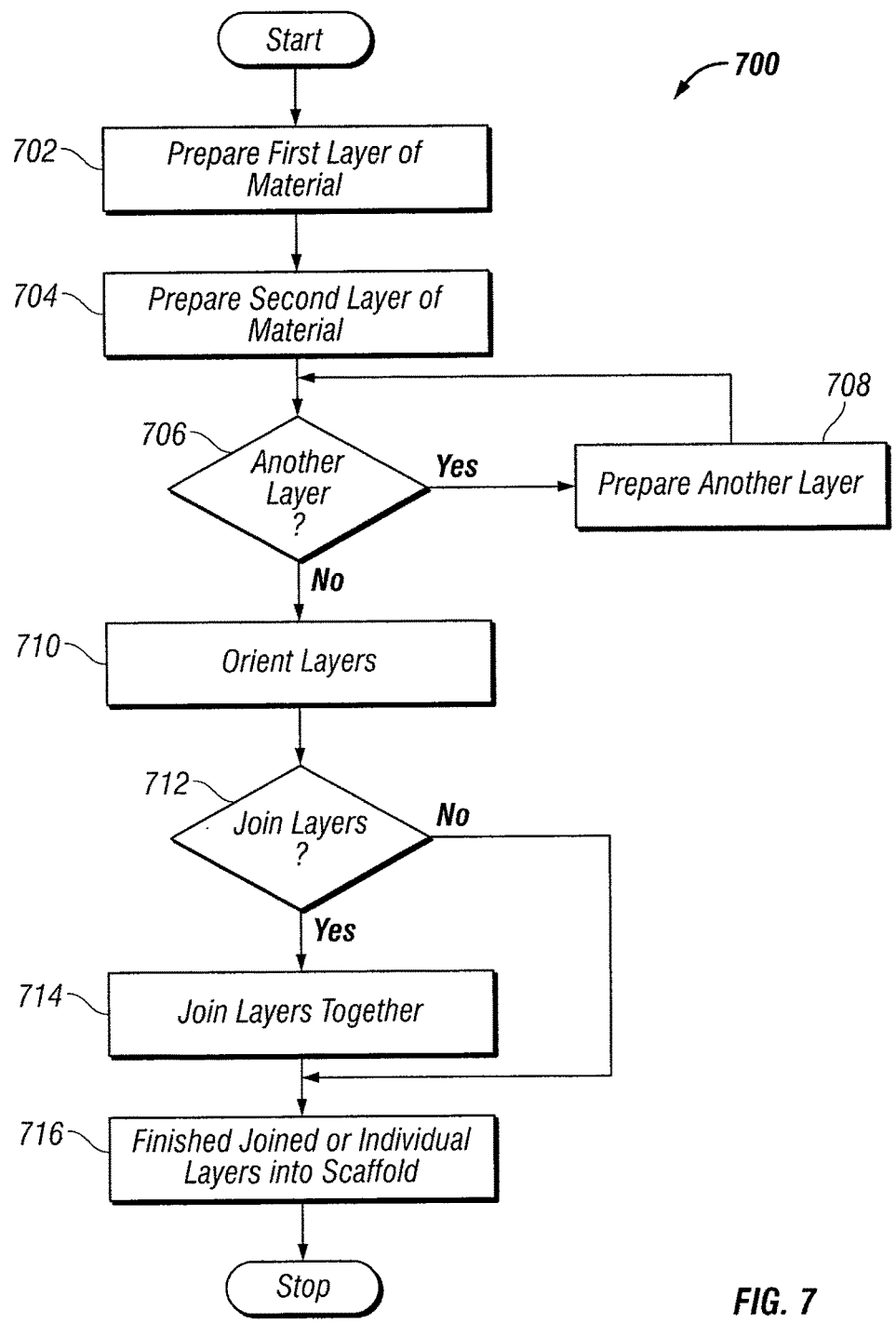
FIG. 7 illustrates a flow chart of an illustrative process for making a fiber-microsphere composite scaffold according to another illustrative embodiment of the invention.

In addition to the aforementioned aspects and illustrative embodiments of the present fiber-microsphere composite scaffold, a method for manufacturing a fiber-microsphere composite scaffold is provided in another illustrative embodiment. FIG. 7 illustrates a flow chart of a process for making a fiber-microsphere composite scaffold 700. In steps 702 and 704, a first layer of material and a second layer of material are prepared according to the disclosure contained herein. The first layer may be one of a fiber layer or a microsphere layer. The second layer then is the other of the fiber layer or microsphere layer. Additionally, as described above, the first and second layers of material may consist of the same type of material and additional layers of material may be different.

In step 706, an inquiry is made as to whether an additional layer of material is desired. If the answer to this inquiry is "yes," then in step 708 another layer of material is prepared. As long as the answer to the inquiry at step 706 is yes, then additional layers of material, either fiber layers or microsphere layers, are prepared. If the answer to the inquiry in step 706 is "no," then in step 710 the layers of material are oriented where in an alternating fashion based on the type of material. For example, if the first layer of material is a fiber layer, then the second layer of material will be a microsphere layer. Likewise, if the second layer of material is a microsphere layer, then a third layer of material may be a fiber layer, and so on. As described herein, adjacent layers of the same type of material may be oriented next to a layer of material of a different type. In step 712, an inquiry is made as to whether the oriented layers are to be joined or otherwise fastened together.

If the answer to the inquiry in step 712 is "yes," then in step 714 the layers are joined together according to the principles disclosed herein. If the answer to the inquiry is "no," then the individual layers of material are finished into a fiber-microsphere composite scaffold. Likewise, in step 714, the joined layers are finished into a fiber-microsphere composite scaffold. In step 716, the finished fiber-microsphere composite scaffold may be shaped, formed, trimmed, cut, or the like to complete its final shape. Additionally, in step 716, any additional manufacturing steps, such as finishing, sterilization, packaging, and the like are performed.

Figure 8:
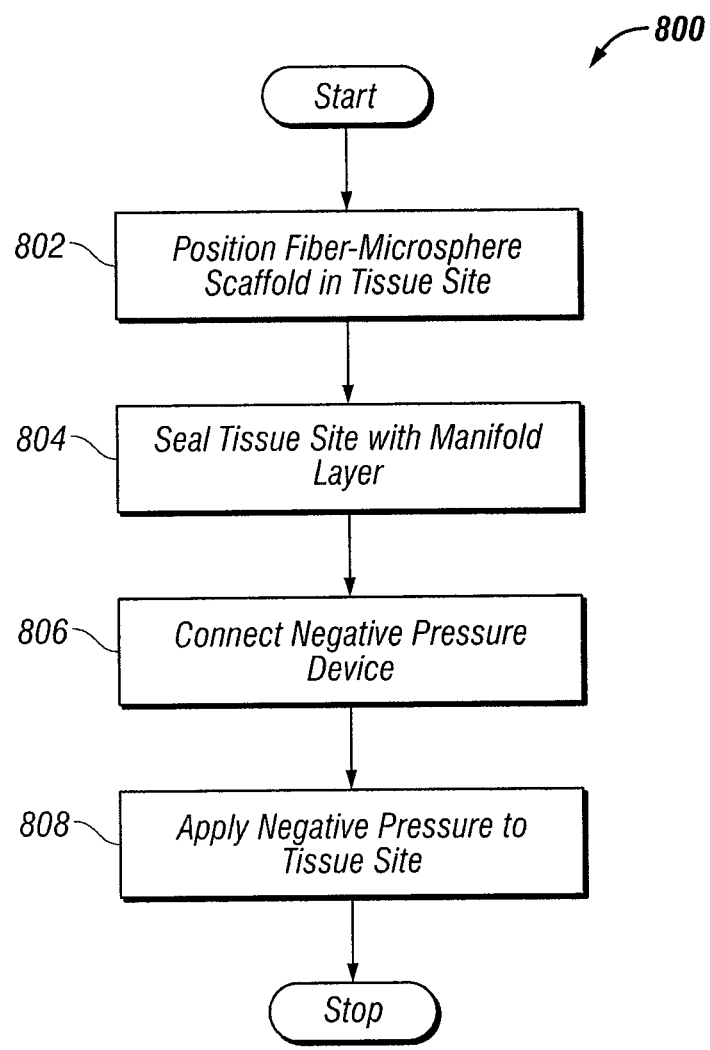
FIG. 8 illustrates a flow chart of an illustrative process for treating a tissue site with a fiber-microsphere composite scaffold reduced pressure tissue treatment apparatus according to an illustrative embodiment of the invention.

FIG. 8 illustrates an illustrative embodiment of a flow chart of an illustrative process for treating a tissue site with a reduced pressure tissue treatment system 800. In step 802, a fiber-microsphere composite scaffold is placed adjacent to a tissue site. In step 804, a manifold is placed over the fiber-microsphere composite scaffold sealing it adjacent tissue of the tissue site. In step 806, a reduced pressure source is connected to the manifold. Finally, in step 808, reduced pressure is applied to the tissue site.

It should be apparent from the foregoing that an invention having significant advantages has been provided. While the invention is shown in only a few of its forms, it is not just limited but is susceptible to various changes and modifications without departing from the spirit thereof.

I claim:

1. A reduced pressure tissue treatment apparatus for applying a reduced pressure tissue treatment to a tissue site comprising:
    a composite scaffold formed from porous materials comprising:
        a first layer of porous material selected from one of a layer of bioresorbable microspheres and a layer of bioresorbable fibers;
        a second layer of porous material selected from the other of said layer of bioresorbable microspheres and said layer of bioresorbable fibers, wherein a substantially planar surface of the first layer is joined to a substantially planer surface of the second layer at an interface, and wherein one of the first layer of material and the second layer of material are adapted to be located substantially adjacent to the tissue site; and
    wherein the porous materials of the first layer and the second layer include a plurality of flow channels formed by openings in the porous materials of the first layer and the second layer, each layer having pore sizes from about 50 microns to about 600 microns, wherein the first layer and the second layer are in fluid communication with adjacent openings to distribute reduced pressure through the composite scaffold to the tissue site while minimizing compression of the composite scaffold to prevent occlusion of the pores when reduced pressure is applied to the composite scaffold; and
    a reduced pressure source fluidly connected to the composite scaffold for supplying reduced pressure to the composite scaffold.

2. The reduced pressure tissue treatment apparatus of claim 1, wherein the composite scaffold further comprises: additional layers of porous material selected from one of said layer of bioresorbable microspheres and said layer of bioresorbable fibers.

3. The reduced pressure tissue treatment apparatus of claim 1, wherein said first layer of porous material and said second layer of porous material are selected from the group consisting of bioresorbable material may be made from polylactide ("PLA") (both L-lactide and D,L-lactide), copolymer of Poly(L-lactide-co-D,L-lactide), polyglycolic acid ("PGA"), alpha esters, saturated esters, unsaturated esters, orthoesters, carbonates, anhydrides, ethers, amides, saccharides, polyesters, polycarbonates, polycaprolactone ("PCL"), polytrimethylene carbonate ("PTMC"), polydioxanone ("PDO"), polyhydroxybutyrate, polyhydroxyvalerate, polyorthoesters, polyphosphazenes, polyurethanes, collagen, hyaluronic acid, chitosan, hydroxyapatite, coralline apatite, calcium phosphate, calcium sulfate, carbonates, bioglass, allografts, autografts, mixtures, and co-polymers of these compounds.

4. The reduced pressure tissue treatment apparatus of claim 1, wherein said first layer of porous material and said second layer of porous material are joined together by at least one of the following means bonding, adhesives, welding, fastening, and sintering.

5. The reduced pressure tissue treatment apparatus of claim 1, wherein said first layer of porous material has a thickness of about 0.1 mm to about 1 mm and the second layer of porous material has a thickness of about 0.2 mm to about 1 mm.

6. The reduced pressure tissue treatment apparatus of claim 1, wherein said layer of bioresorbable microspheres are sintered together.

7. The reduced pressure tissue treatment apparatus of claim 1, wherein the openings of the plurality of flow channels are selected from the group consisting of pores, voids, apertures, and cells.

8. The reduced pressure tissue treatment apparatus of claim 1, wherein the layer of bioresorbable fibers includes fibers comprising thread filaments.

9. The reduced pressure tissue treatment apparatus of claim 8, wherein the fibers are continuous filaments or discrete elongated filaments.

10. The reduced pressure tissue treatment apparatus of claim 8, wherein the fibers are microfibers.

11. The reduced pressure tissue treatment apparatus of claim 8, wherein the fibers are natural filaments or synthetic filaments.

12. A reduced pressure tissue treatment apparatus for applying a reduced pressure tissue treatment to a tissue site comprising:
    a first layer of porous material selected from one of a layer of bioresorbable microspheres and a layer of bioresorbable fibers;
    a second layer of porous material selected from the other of said layer of bioresorbable microspheres and said layer of bioresorbable fibers, wherein a substantially planar surface of said first layer is joined to a substantially planer surface of said second layer at an interface, and wherein one of said first layer of material and said second layer of material are adapted to be located substantially adjacent to said tissue site;
    a manifold located substantially over said first layer and said second layer in sealing communication with said tissue site to receive reduced pressure for the tissue site; and
    wherein the porous materials of the first layer and the second layer include a plurality of flow channels formed by openings in the porous materials of the first layer and the second layer in fluid communication with adjacent openings to distribute a reduced pressure through said manifold to said tissue site, and wherein the openings of the plurality of flow channels are pores having pore sizes from about 50 microns to about 600 microns to minimize compression of the composite scaffold and prevent occlusion of the pores when reduced pressure is applied to the composite scaffold.

13. The reduced pressure tissue treatment apparatus of claim 12, further comprising:
additional layers of porous material selected from one of said layer of bioresorbable microspheres and said layer of bioresorbable fibers located adjacent to one of said first layer of porous material and said second layer of porous material.

14. The reduced pressure tissue treatment apparatus of claim 12, wherein said first layer of porous material and said second layer of porous material are selected from the group consisting of bioresorbable material may be made of polylactide ("PLA") (both L-lactide and D,L-lactide), copolymer of Poly(L-lactide-co-D,L-lactide), polyglycolic acid ("PGA"), alpha esters, saturated esters, unsaturated esters, orthoesters, carbonates, anhydrides, ethers, amides, saccharides, polyesters, polycarbonates, polycaprolactone ("PCL"), polytrimethylene carbonate ("PTMC"), polydioxanone ("PDO"), polyhydroxybutyrate, polyhydroxyvalerate, polyorthoesters, polyphosphazenes, polyurethanes, collagen, hyaluronic acid, chitosan, hydroxyapatite, coralline apatite, calcium phosphate, calcium sulfate, carbonates, bioglass, allografts, autografts, mixtures, and co-polymers of these compounds.

15. A process of making a fiber-microsphere composite scaffold comprising:
preparing a first layer of porous material selected from one of a layer of bioresorbable microspheres and a layer of bioresorbable fibers having a plurality of flow channels formed by openings in the porous material of the first layer in fluid communication with adjacent openings to distribute reduced pressure, and wherein the openings in the porous material have pore sizes from about 50 microns to about 600 microns to minimize compression of the composite scaffold and prevent occlusion of the pores when reduced pressure is applied to the composite scaffold;
preparing a second layer of porous material selected from the other of said layer of bioresorbable microspheres and said layer of bioresorbable fibers having a plurality of flow channels formed by openings in the porous material of the second layer in fluid communication with adjacent openings to distribute reduced pressure, and wherein the openings in the porous material have pore sizes from about 50 microns to about 600 microns to minimize compression of the composite scaffold and prevent occlusion of the pores when reduced pressure is applied to the composite scaffold;
orienting said first layer of porous material and said second layer of porous material
joining a substantially planar surface of the first layer is to a substantially planer surface of the second layer at an interface; and
finishing said fiber-microsphere composite scaffold.

16. The process for making a fiber-microsphere composite scaffold of claim 15, further comprising:
preparing additional layers of porous material selected from one of said layer of bioresorbable microspheres and said layer of bioresorbable fibers.

17. The process for making a fiber-microsphere composite scaffold of claim 16, further comprising:
joining said additional layers of porous material to said first layer of material and said second layer of material.

18. The process for making a fiber-microsphere composite scaffold of claim 16, wherein finishing said fiber-microsphere composite scaffold comprises:
processing said fiber-microsphere composite scaffold by at least one of shaping, trimming, cutting, forming, sterilizing, and packaging.

19. The process for making a fiber-microsphere composite scaffold of claim 15, wherein said joining comprises at least one process selected from the group consisting of welding, bonding, adhering, gluing, ultrasonic point-bonding, fastening, and pressing.

20. A reduced pressure tissue treatment apparatus for applying a reduced pressure tissue treatment to a tissue site comprising:
a composite scaffold formed from porous materials comprising:
a first layer of porous material selected from one of a layer of bioresorbable microspheres and a layer of bioresorbable fibers;
a second layer of porous material selected from the other of said layer of bioresorbable microspheres and said layer of bioresorbable fibers, wherein a substantially planar surface of the first layer is joined to a substantially planer surface of the second layer at an interface, and wherein one of the first layer of material and the second layer of material are adapted to be located substantially adjacent to the tissue site; and
wherein the porous materials of the first layer and the second layer include a plurality of flow channels formed by openings in the porous materials of the first layer and the second layer, each layer having pore sizes from about 400 microns to about 600 microns, wherein the first layer and the second layer are in fluid communication with adjacent openings to distribute reduced pressure through the composite scaffold to the tissue site, while minimizing compression of the composite scaffold to prevent occlusion of the pores when reduced pressure is applied to the composite scaffold; and
a reduced pressure source fluidly connected to the composite scaffold for supplying reduced pressure to the composite scaffold.

21. A reduced pressure tissue treatment apparatus for applying a reduced pressure tissue treatment to a tissue site comprising:
a first layer of porous material selected from one of a layer of bioresorbable microspheres and a layer of bioresorbable fibers;
a second layer of porous material selected from the other of said layer of bioresorbable microspheres and said layer of bioresorbable fibers, wherein a substantially planar surface of said first layer is joined to a substantially planer surface of the said second layer at an interface one of said first layer of material and said second layer of material are adapted to be located substantially adjacent to said tissue site;
a manifold located substantially over said first layer and said second layer in sealing communication with said tissue site to receive reduced pressure for the tissue site; and
wherein the porous materials of the first layer and the second layer include a plurality of flow channels formed by openings in the porous materials of the first layer and the second layer in fluid communication with adjacent openings to distribute a reduced pressure through said manifold to said tissue site, and wherein the openings of the plurality of flow channels are pores having pore sizes from about 400 microns to about 600 microns to minimize compression of the composite scaffold and prevent occlusion of the pores when reduced pressure is applied to the composite scaffold.

* * * * *